United States Patent
Fancher

[11] 3,956,430
[45] May 11, 1976

[54] DITHIOPHOSPHATE AND DITHIOPHOSPHONATES

[75] Inventor: Llewellyn W. Fancher, Orinda, Calif.

[73] Assignee: Stauffer Chemical Company, Westport, Conn.

[22] Filed: Feb. 21, 1975

[21] Appl. No.: 550,260

[52] U.S. Cl. .............................. 260/949; 260/609 E; 260/609 F; 71/87; 424/216
[51] Int. Cl.² ..................... C07F 9/165; C07F 9/40; A01N 9/36
[58] Field of Search .................................. 260/949

[56] References Cited
UNITED STATES PATENTS

| | | | |
|---|---|---|---|
| 3,060,217 | 10/1962 | Schrader | 260/949 |
| 3,865,905 | 2/1975 | Fancher | 260/949 |

Primary Examiner—Anton H. Sutto
Attorney, Agent, or Firm—Edwin H. Baker

[57] ABSTRACT

Compounds of the formula

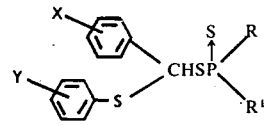

in which R is alkoxy having 1 to 5 carbon atoms; $R^1$ is alkyl having 1 to 5 carbon atoms or alkoxy having 1 to 5 carbon atoms; X is hydrogen, chlorine, bromine, methyl, methoxy or ethoxy and Y is hydrogen, chlorine, bromine, methyl, methoxy or ethoxy as insecticides, acaricides or herbicides.

3 Claims, No Drawings

DITHIOPHOSPHATE AND DITHIOPHOSPHONATES

This invention relates to the use of certain novel chemical compounds as insecticides, acaricides or herbicides, more particularly the chemical compounds are certain dithiophosphates and dithiophosphonates.

The compounds of the present invention that are useful as insecticides, acaricides or herbicides are those having the formula

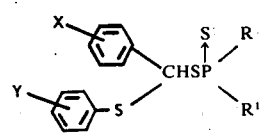

in which R is alkoxy having 1 to 5 carbon atoms, preferably ethyl; R¹ is alkyl having 1 to 5 carbon atoms, preferably ethyl, or alkoxy having 1 to 5 carbon atoms, preferably ethoxy; X is hydrogen, chlorine, bromine, methyl, methoxy or ethoxy and Y is hydrogen, chlorine, bromine, methyl, methoxy or ethoxy.

The compounds having the formula

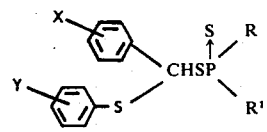

in which R, R¹, X and Y are as defined can be prepared by the following reactions:

Reaction 1

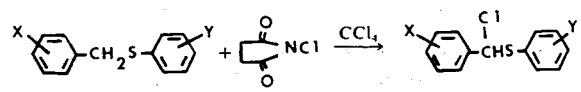

Reaction 2

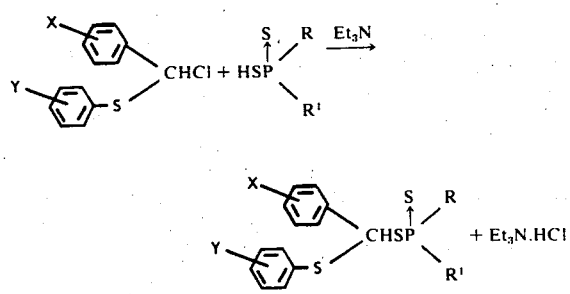

Preferably, reaction number 1 is carried out in the manner taught in J. Org. Chem., 32 (1967) pages 204-206 and 4006-4008, utilizing the appropriately substituted benzyl phenyl sulfide when such substitution is desired.

Preferably, reaction number 2 is carried out by dissolving the dithioacid in a solvent such as benzene, then neutralized with Et₃N below 30°C. The reaction product obtained from reaction number 1 is dissolved in the solvent and added to the other solution at about 15°C. After an exothermic reaction, the mixture is heated to reflux for about 90 minutes. The reaction product is recovered from the reaction mixture and purified by conventional means, such as diluting with solvent, washing with $H_2O$, then with dilute $NaHCO_3$ and twice again with $H_2O$. The product is dried over $MgSO_4$, filtered and distilled in vacuum.

Preparation of the compounds of this invention is illustrated by the following examples.

EXAMPLE I

α-O,O-diethylphosphorodithioylbenzylphenyl sulfide 17.9 grams (0.096 mole) $(C_2H_5O)_2P(S)SH$ is dissolved in 25 cc. benzene and then neutralized below 30°C. with $(C_2H_5)_3N$ (a few extra drops are added to raise pH to 7.5). (0.06 mole) 14.1 grams α-chlorobenzoyl-phenyl sulfide, dissolved in 25 cc. benzene, is added at 15°C. The temperature rises to 39°C. The mixture is heated on a steam bath with refluxing for about 90 minutes. The reaction product is cooled, diluted with benzene and washed with water. It is then washed with dilute $NaHCO_3$ twice with $H_2O$ and dried over $MgSO_4$. The product is recovered by filtering and evaporating the solvent. The yield is 20 grams, 87% yield of the desired product is obtained $N_{30}^D = 1.5959$.

The following is a table of certain selected compounds that are preparable according to the procedure described hereto. Compound numbers are assigned to each compound and are used throughout the remainder of the application.

TABLE I

| Compound Number | R | R¹ | X | Y |
|---|---|---|---|---|
| 1 | $C_2H_5O$ | $C_2H_5O$ | H | 4-Cl |
| 2 | $CH_3O$ | $CH_3O$ | H | 4-Cl |
| 3ᵃ | $C_2H_5O$ | $C_2H_5O$ | H | H |
| 4 | $CH_3O$ | $CH_3O$ | H | H |
| 5 | $CH_3O$ | $C_2H_5$ | H | 4-Cl |
| 6 | $i-C_3H_7O$ | $C_2H_5$ | H | 4-Cl |
| 7 | $C_2H_5O$ | $C_2H_5$ | H | 4-Cl |
| 8 | $CH_3O$ | $C_2H_5$ | 4-Cl | H |
| 9 | $i-C_3H_7O$ | $i-C_3H_7O$ | 4-Cl | H |

TABLE I-continued

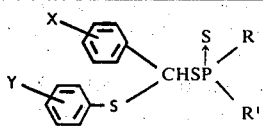

| Compound Number | R | R¹ | X | Y |
|---|---|---|---|---|
| 10 | $C_2H_5O$ | $C_2H_5O$ | 3-$CH_3$ | H |
| 11 | $CH_3O$ | $CH_3O$ | 3-$CH_3$ | H |
| 12 | $C_2H_5O$ | $C_2H_5O$ | H | 4-$CH_3O$ |
| 13 | $CH_3O$ | $CH_3O$ | H | 4-$CH_3O$ |
| 14 | $C_2H_5O$ | $C_2H_5O$ | 2-Cl | H |
| 15 | $CH_3O$ | $CH_3O$ | 2-Cl | H |

ªPrepared in Example 1.

The following tests illustrate utility of the compounds as insecticides and acaricides.

INSECTICIDAL EVALUATION TESTS

The following insect species were used in evaluation tests for insecticidal activity:
1. Housefly (HF) — *Musca domestica* (Linn.)
2. Lygus Bug (LB) — *Lygus hesperus* (Knight)
3. Bean Aphid (BA) — *Aphis fabae* (Scop.)

The housefly (HF) was used in evalutaion tests of selected compounds as insecticides by the following procedure. A stock solution containing 100 µg/ml. of the toxicant in an appropriate solvent was prepared. Aliquots of this solution were combined with 1 milliliter of an acetone-peanut oil solution in a glass Petri dish and allowed to dry. The aliquots were there to achieve desired toxicant concentration ranging from 100 µg per Petri dish to that at which 50% mortality was attained. The Petri dishes were placed in a circular cardboard cage, closed on the bottom with cellophane and covered on top with cloth netting. Twenty-five female houseflies, 3 to 5 days old, were introduced into the cage and the present mortality was recorded after 48 hours. The LD–50 values are expressed in terms µg per 25 female flies. The result of this insecticidal evaluation tests are given in Table II under "HF".

In the Lygus Bug (LB) *Lygus hesperus* test 25 insects were placed in circular cardboard cages sealed on one end with cellophane and covered by a cloth netting on the other. Aliquots of the toxicants, dissolved in an appropriate solvent, were diluted in water containing 0.002% of a wetting agent, Sponto 221 (a polyoxyether of alkylated phenols blended with organic sulfonates). The caged insects were sprayed with the candidate compounds at concentrations ranging from 0.05% downward to that at which 50% mortality was obtained through the cloth netting by means of a hand spray gun. After 24 and 72 hours, counts were made to determine living and dead insects. The LD–50 (Percent) values were calculated. These values are reported under the column "LB" in Table II.

The insect species black bean aphid (BA) *Aphis fabae* (Scop.) was also employed in the test for insecticidal activity. Young nasturitum (Tropaeolum sp.) plants, approximately 2 to 3 inches tall, were used as the host plants for the bean aphid. The host plant was infested with approximately 50–75 of the aphids. The test chemical was dissolved in acetone, added to water which contained a small amount of Sponto 221, an emulsifying agent. The solution was applied as a spray to the infested plants. Concentrations ranged from 0.05 percent downward until an LD–50 value was achieved. These results are given in Table II under the column "BA".

ACARICIDAL EVALUATION TEST

The two-spotted mite (2SM), *Tetranychus urticae* (Koch), was employed in tests for miticides. Young pinto bean plants or lima bean plants (Phaseolus s.p.) in the primary leaf stage were used as the host plants. The young pinto bean plants were infested with about 100 mites of various ages. Dispersions of candidate materials were prepared by dissolving 0.1 gram in 10 ml. Of a suitable solvent, usually acetone. Aliquots of the toxicant solutions were suspended in water containing 0.002% v/v Sponto 221, polyoxy-ethylene ether sorbitan monolaurate, an emulsifying agent, the amount of water being sufficient to give concentrations of active ingredient ranging from 0.05% to that at which 50% mortality was obtained. The test suspensions were then sprayed on the infested plants to the point of run off. After 7 days, mortalities of post-embryonic and ovicidal forms were determined. The percentage of kill was determined by comparision with control plants which had not been sprayed with the candidate compounds. The LD–50 values were calculated using well-known procedures. These values are reported under the columns "2SM-PE" and "2SM-Eggs" in Table II.

TABLE II

| Compound Number | HF µg | LB % | BA % | PE % | 2SM EGGS % |
|---|---|---|---|---|---|
| 1 | 75 | — | .008 | .03 | .05 |
| 3 | 30 | .05 | .005 | .005 | .03 |
| 5 | — | — | .05 | .05 | — |
| 6 | 80 | .05 | .008 | .03 | — |
| 7 | 30 | — | .005 | .001 | .01 |
| 8 | 30 | — | .05 | .008 | .008 |
| 10 | — | .05 | — | — | — |
| 14 | 30 | .05 | .003 | .008 | .03 |
| 15 | 60 | — | .03 | .05 | — |

HERBICIDAL SCREENING TEST

AS previously mentioned, the herein described compounds produced in the above-described manner are phytotoxic compounds which are useful and valuable in controlling various plant species. Selected compounds of this invention are tested as herbicides in the following manner.

Pre-emergence herbicide tests

On the day preceding treatment, seeds of seven different weed species are planted in individual rows using one species per row across the width of the flat. The seeds used are hairy crabgrass (*Digitaris sanguinalis* (L.) Scop.), yellow foxtail (*Setaria glauca* (L.) Beauv.), watergrass (*Echinochlea crusgalli* (L.) Beauv.), California red oat (*Avena sativa* (L.)), redroot pigweed (*Amaranthus retroflexus* (L.)), indian mustard (*Brassica juncea* (L.) Coss.) and curly dock (*Rumex crispus* (L.)). Ample seeds are planted to give about 20 to 50 seedlings per row, after emergence, depending upon the size of the plants. The flats are watered after planting. The spraying solution is prepared by dissolving 50 mg. of the test compound in 3 ml. of a solvent, such as acetone, containing 1% Tween 20 (polyoxyethylene sorbitan monolaurate). The following day each flat is sprayed at the rate of 20 pounds of the candidate compound per 80 gallons of solution per acre. An atomizer is used to spray the solution onto the soil surface. The flats are placed in a greenhouse at 80°F. and watered regularly. Two weeks later the degree of weed control is determined by comparing the amount of germination and growth of each weed in the treated flats with the same weeds in several untreated control flats. The rating system is as follows:

− = no significant injury (0 – 15 percent control)
+ = slight injury (25 – 35 percent control)
++ = moderate injury (55 – 65 percent control)
+++ = severe injury or death (85 – 100 percent control)

An activity index is used to represent the total activity of all seven weed species. It is the sum of the number of plus marks, so that an activity index of 21 represents almost complete control of all seven weeds. The results of this test are reported in Table III.

Post-emergence herbicide test

Seeds of five weed species including hairy crabgrass, watergrass, California red oats, Indian mustard, and curly dock and one crop, pinto beans (*Phaseolus vulgaris*), are planted in flats as described above for pre-emergence screening. The flats are placed in the greenhouse at 72°–85°F. and watered daily with a sprinkler. About 10 to 14 days after planting when the primary leaves of the bean plant are almost fully expanded and the first trifoliate leaves are just starting to form, the plants are sprayed. The spray is prepared by weighing out 50 mg. of the test compound, dissolving it in 5 ml. of acetone containing 1% Tween 20 (polyoxyethylene sorbitan monolaurate) and then adding 5 ml. of water. The solution is sprayed on the foliage using an atomizer. The spray concentration is 0.5% and the rate would be approximately 20 pounds per acre if all of the spray was retained on the plant and the soil, but some spray is lost so it is estimated that the application rate is approximately 12.5 pounds per acre.

Beans are used to detect defoliants and plant growth regulators. The beans are trimmed to two or three plants per flat by cutting off the excess weaker plants several days before treatment. The treated plants are placed back in the greenhouse and care is taken to avoid sprinkling the treated foliage with water for three days after treatment. Water is applied to the soil by means of a slow stream from a watering hose taking care not to wet the foliage.

Injury rates are recorded 14 days after treatment. The rating system is the same as described above for the pre-emergence test where (−), (+), (++), and (+++) are used for the different rates of injury and control. The injury symptons are also recorded. The maximum activity index for complete control of all the species in the post-emergence screening test is 18 which represents the sum of the plus marks obtained with the six plant species used in the test. The herbicide activity is shown in Table III.

TABLE III

| Compound Number | HERBICIDAL ACTIVITY SCREENING RESULTS Herbicidal Activity Index** | |
|---|---|---|
| | Pre-emergence (20 lb/A) | Post-emergence (12.5 lb./A) |
| 1 | 0 | 7 |
| 2 | 0 | 12 |
| 3 | 0 | 3 |
| 4 | 0 | 6 |
| 5 | 0 | 0 |

TABLE III-continued

| Compound Number | HERBICIDAL ACTIVITY SCREENING RESULTS Herbicidal Activity Index** | |
|---|---|---|
| | Pre-emergence (20 lb/A) | Post-emergence (12.5 lb./A) |
| 6 | 0 | 0 |
| 7 | 0 | 0 |
| 8 | 2 | 4 |
| 9 | 0 | 0 |
| 10 | 0 | 4 |
| 11 | 6 | 7 |
| 12 | 5 | 7 |
| 13 | 7 | 8 |
| 14 | 0 | 1 |
| 15 | 0 | 1 |

**21 = 85–100% of all seven plant species tested pre-emergence.
18 = 85–100% of all six plant species tested post-emergence.

The compounds of the present invention can be applied in a variety of ways of various concentrations. In practice, the compounds are formulated into pesticidal compositions, by admixture, in pesticidally effective amounts, with the adjuvants and carriers normally employed for facilitating the dispersion of active ingredients for agricultural applications, considering that the formulation and mode of application of a toxicant may affect the activity of the material in a given application.

More specifically, the active compounds may be formulated as granules of relatively large particle size, as wettable powders, as emulsifiable concentrates, as powdery dusts, as solutions or as any of several other known types of formulations, depending upon the desired mode of application. These formulations may contain as little as about 0.5% to as much as about 95% or more by weight of active ingredient. The amount applied depends upon the nature of the pests to be controlled.

Wettable powders are in the form of finely divided particles which disperse readily in water or other dispersant. The wettable powder is ultimately applied either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient by weight and usually also contain a small amount of wetting, dispersing or emulsifying agent to facilitate wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphthas, isophorone and other non-volatile organic solvents. For herbicidal application, these concentrates are dispersed in water or other liquid carrier and normally applied as a spray to the area to be treated.

Granular formulations, wherein the toxicant is carried on relatively coarse particles, are usually applied without dilution to the area in which suppression of vegetation is desired. Typical carriers for granular formulations include sand, fuller's earth, bentonite clays, vermiculite, perlite, and other organic or inorganic materials which absorb or which may be coated with the toxicant. Granular formulations normally are prepared to contain about 5% to about 25% of active ingredients which may include surface-active agents such as wetting agents, dispersing agents or emulsifiers;

oils such as heavy aromatic naphthas, kerosene or other petroleum fractions, or vegetable oils; and/or stickers such as dextrins, glue or synthetic resins.

Typical wetting, dispersing or emulsifying agents used in agricultural formulations include, for example, the alkyl and alkylaryl sulfonates and sulfates and their sodium salts; polyhydric alcohols; and other types of surface-active agents, many of which are available in commerce. The surface-active agent, when used, normally comprises from 0.1% to 15% by weight of the herbicidal composition.

Dusts, which are free-flowing admixtures of the active ingredient with finely divided solids such as talc, clays, flours, and other organic and inorganic solids which act as dispersants and carriers for the toxicant, are useful formulations for soil-incorporating applications.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

Other useful formulations for pesticidal applications include simple solutions of the active ingredient in a dispersant in which it is completely soluble at the desired concentration, such as acetone, alkylated naphthalenes, xylene or other organic solvents. Pressurized sprays, typically aerosols, wherein the active ingredient is dispersed in finely-divided form as a result of vaporization of a low boiling dispersant solvent carrier, such as the Freons, may also be used.

The pesticidal compositions can be applied in the conventional manner. Thus, the dust and liquid compositions can be applied by the use of power-dusters, boom and hand sprayers and spray dusters. The compositions can also be applied from airplanes as a dust or a spray because they are effective in very low dosages.

In order to modify or control growth of germinating seeds or emerging seedlings, as a typical example, the dust and liquid compositions are applied to the soil according to convention methods and are distributed in the soil to a depth of at least ½ inch below the soil surface. It is not necessary that the phytotoxic compositions be admixed with the soil particles since these compositions can also be applied merely by spraying or sprinkling the surface of the soil. When used as herbicides, dust compositions, granular compositions or liquid formulations can be applied to the surface of the soil and then distributed below the surface of the soil by conventional means such as discing, dragging or mixing operations.

What is claimed is:
1. A compound having the formula

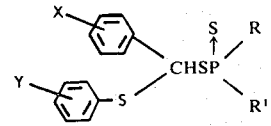

in which R is alkoxy having 1 to 5 carbon atoms; $R^1$ is alkyl having 1 to 5 carbon atoms; or alkoxy having 1 to 5 carbon atoms; X is hydrogen, chlorine, bromine, methyl, methoxy, or ethoxy and Y is hydrogen, chlorine, bromine, methyl, methoxy or ethoxy.

2. The compound of claim 1 in which R is ethoxy, $R^1$ is ethoxy, X is hydrogen and Y is hydrogen.

3. The compound of claim 1 in which R is methoxy, $R^1$ is methoxy, X is hydrogen and Y is 4-chloro.

* * * * *